United States Patent [19]
Munetaka

[11] Patent Number: 6,029,495
[45] Date of Patent: Feb. 29, 2000

[54] ANALYZING SYSTEM

[75] Inventor: Keisuke Munetaka, Kyoto, Japan

[73] Assignee: Shimadzu Corporation, Kyoto, Japan

[21] Appl. No.: 09/080,930

[22] Filed: May 19, 1998

[30] Foreign Application Priority Data

May 21, 1997 [JP] Japan ..................................... 9-148663

[51] Int. Cl.[7] ........................... G01N 15/06; G01D 18/00
[52] U.S. Cl. ............................................. 73/1.02; 250/574
[58] Field of Search ............................ 250/574; 356/326, 356/337; 73/1.02, 53.01

[56] References Cited

U.S. PATENT DOCUMENTS

| | | | |
|---|---|---|---|
| 5,022,980 | 6/1991 | Tanaka et al. | ........................... 204/400 |
| 5,691,920 | 11/1997 | Levine et al. | ........................... 702/186 |

*Primary Examiner*—Edward P. Westin
*Assistant Examiner*—Glenn T Kinnear

*Attorney, Agent, or Firm*—Armstrong, Westerman, Hattori, McLeland & Naughton

[57] ABSTRACT

In an inventive analyzing system (e.g. liquid chromatograph), an analyzing schedule includes data on whether or not to carry out a self-check for each sample, and data on what process to follow the self-check according to the check result, in addition to data on the analyzing order and analyzing condition of a series of analyses on a plurality of samples. In carrying out the analysis according to the schedule, a self-check is carried out after an analysis of a sample for which the self-check is scheduled. In the self-check, a data collecting unit 17 collects data on the degree of degradation of expendable parts and on the wavelength error of a spectrophotometric detector 14, etc., and a checking unit 18 detects abnormality by comparing the data to preset tolerable values. For example, in the case where the process specified to follow the detection of abnormality is "stop analysis on detecting abnormality", a control unit 15 stops each part of the system so that the rest of the analyses are deferred.

10 Claims, 2 Drawing Sheets

| Serial No | Sample Name | Sample Type | Method File Name | Self Check | Process to follow |
|---|---|---|---|---|---|
| 1 | a | Unknown | Sample1.Met | No | |
| 2 | b | Unknown | Sample2.Met | Yes | Stop analysis on detecting abnormality |
| 3 | c | Standard | Sample3.Met | Yes | Disregard check result |
| 4 | d | Unknown | Sample4.Met | Yes | Suspend analysis on detecting abnormality |
| 5 | e | Standard | Sample5.Met | No | |
| ⋮ | ⋮ | ⋮ | ⋮ | ⋮ | ⋮ |

ANALYZING SYSTEM

The present invention relates to an analyzing system which carries out a series of analyses on a plurality of samples, automatically selecting one sample from another. Particularly, the present invention relates to an analyzing system having a self-check system for automatically detecting abnormality in itself In the following description, a liquid chromatograph is taken as an example of analyzing systems to which the present invention is applicable. It should be appreciated hereby that the present invention is also applicable to gas chromatographs, for example, and to other types of analyzing systems used in various fields.

BACKGROUND OF THE INVENTION

FIG. 3 shows a schematic configuration of a conventionally used liquid chromatograph (LC). In the LC, eluent from a liquid supply unit 11 is supplied to a column 13 at a preset flow rate. An automatic injector 12 selects one sample after another from a plurality of liquid samples (not shown) in a predetermined order, extracts a preset quantity of the liquid sample selected, and injects the liquid sample into the eluent. The liquid sample injected in the eluent is carried into the column 13 by the eluent. While flowing through the column 13, the liquid sample is separated into components due to difference in the retention time. The components in the eluate from the column 13 are detected by a detector 14, which sends detection signals to a data processing unit 16. The type of detector 14 to be used is determined according to the object for the analysis. For example, a spectrophotometric detector, a fluorophotometric detector or an electric conductivity detector, is generally used as the detector 14. The data processing unit 16 processes the detection signals to build a chromatogram for each sample, and carries out qualitative analysis and/or quantitative measurement of the components by analyzing the chromatogram. A control unit 15 controls the operations of the above-described units according to an analyzing condition which is preset by the operator. A managing unit 20, consisting of a personal computer (PC) and other peripheral devices, performs several functions, such as: creating and maintaining files containing data of processing conditions, analyzing conditions, etc.; sending predetermined control signals to the control unit 15 and the data processing unit 16; and creating, saving and maintaining files containing data of the result of analysis obtained by the data processing unit 16.

Some of the parts used in the above-described LC are expendable parts, each of which is required to be replaced with a new one after the end of a limited period of time during which the part functions reliably. Sealants for preventing leakage of liquid, such as a plunger seal used in the pump of the liquid supply unit 11 and a needle seal used in the automatic injector 12, and a lamp used in the light source of a spectrophotometric detector, are examples of expendable parts. Usually, the manufacturer of every expendable part specifies the reliable working time usage limit of its product, during which the part is guaranteed to function reliably, and recommends operators to replace such parts prior to the expiration of their useable working life. The total time usage of a part is equal to the total operating time of the unit in which the part is used. For example, the time usage of the plunger seal used in the above-described pump is obtained by integrating the operating time of the liquid supply unit 11, where the integration of time is started when a new plunger seal is put in the liquid supply unit 11.

When a spectrophotometric detector is used as the detector 14 of the LC, the identification of components in the eluate and other analysis become unreliable if wavelength error occurs due to the error in the arrangement of parts of the dispersing mechanism, or due to some other errors. Therefore, a spectrophotometric detector is provided with a checking function for detecting the displacement of the wavelength actually observed from the desired wavelength preset by the operator.

In the above-described LC, the checks on the time usage of each expendable part, the accuracy of wavelength, etc., are carried out only when the operator gives a predetermined instruction to the control unit 15 or the managing unit 20. The check results (e.g. the time usage of each expendable part, the wavelength displacement, etc.) are shown in predetermined forms on displays (not shown) provided to the units, respectively. Based on the check results, the operator judges whether there is any expendable part required to be replaced, and whether the wavelength error is smaller than a preset tolerable limit. The operator carries out the tuning or the like of the spectrophotometric detector if the wavelength displacement is larger than the tolerable limit.

For assisting the operator with making the above-described judgment, the LC is provided with a software program for making a report of the check results. That is, when the program is run on the PC of the managing unit 20, all the data of the check results (the time usage of each of the expendable parts, the wavelength displacement, etc.) are shown in the form of a list. Using the software program, the operator can check whether the analyzing system is in an appropriate condition before or after a series of analyses.

In the above-described LC, a plurality of liquid samples are loaded into the automatic injector 12, and a series of analyses are carried out, automatically selecting one sample after another. As a result, it inevitably takes a very long time to complete all of the series of analyses, which is usually in the order of several hours and sometimes as long as several days. Therefore, it is highly probable that, in the midst of a series of analyses, the total time usage of an expendable part exceeds the time usage limit of the part, or the wavelength error of a spectrophotometric detector becomes larger than a preset tolerable limit. Particularly, the wavelength error is liable to exceed the tolerable limit because it is significantly influenced by environmental conditions (temperature, humidity, etc.). Accordingly, it is probable that the wavelength error exceeds the tolerable limit only in a limited period of time during a series of analyses, and again becomes smaller than the tolerable limit by the end of all the analyses.

In conventional analyzing systems of the above-described type, however, the operator cannot check the condition of the analyzing system in the midst of a series of analyses. Therefore, judgment on the reliability of the result of analysis depends principally on the result of the check carried out before the start of or after the end of the series of analyses. Using such an analyzing system is problematic in respect of reliability when the analysis is uninterruptedly continued for a very long period of time.

SUMMARY OF THE INVENTION

For addressing the above-described problem, the present invention proposes a novel analyzing system which automatically checks the reliability of results of a series of analyses continued for a long period of time.

Thus, the present invention proposes an analyzing system for carrying out a series of analyses on a plurality of samples according to a predetermined analyzing schedule, which includes:

a) an input device for allowing an operator to set the analyzing schedule, where the analyzing schedule includes an option whether or not to carry out a check at an analysis on each of the plurality of samples, and an option of a process to follow the check according to a result of the check;

b) a checking unit for checking a state of a part in the analyzing system at an analysis of a sample at which the check is scheduled to be carried out; and c) a control unit for receiving the result of the check from the checking unit, and for performing the process specified in the analyzing schedule.

In the present invention, the object of the check by the checking unit is, for example, the total time usage of an expendable part used in the analyzing system which is required to be replaced regularly, or the state of a part whose properties (precision, output level, etc.) are liable to change due to a change in environmental conditions, due to a mechanical shock or with the lapse of time.

In using the inventive analyzing system, the operator sets the analyzing schedule for each of a plurality of samples through the input device, in addition to determining the order of analyzing the samples and setting other parameters relevant to the analysis beforehand. That is, in setting the analyzing schedule, the operator determines for what sample the check is to be carried out and what type of process should follow the check according to the result of the check. The type of the process is selected from predetermined items, such as stopping analysis on detecting an abnormality, continuing analysis even on detecting an abnormality, etc., for example.

After starting a series of analyses according to the analyzing schedule, the checking unit collects data on the operation or condition of a specific part in the analyzing system before or after the analysis on a sample for which the check is scheduled. Then, the checking unit checks whether the operation or condition of the part is normal by comparing the data to a preset reference value (maximum tolerable value, for example). Referring to the check result, the control unit controls parts of the analyzing system so that the process scheduled to follow the check result is carried out. For example, when the analysis is scheduled to be stopped on detecting an abnormality, the control unit stops each part of the analyzing system if it is found from the check result that an abnormality has been detected. When the analysis is scheduled to be continued even on detecting an abnormality, on the other hand, the control unit controls each part of the analyzing system to run as it does even if it is found from the check result that an abnormality has been detected.

Accordingly, when the check is scheduled to be carried out for the analysis of every sample, the state of the specific part in the analyzing system is checked every time the sample is replaced with a new one.

DETAILED DESCRIPTION OF A PREFERRED EMBODIMENT

Figure 1:
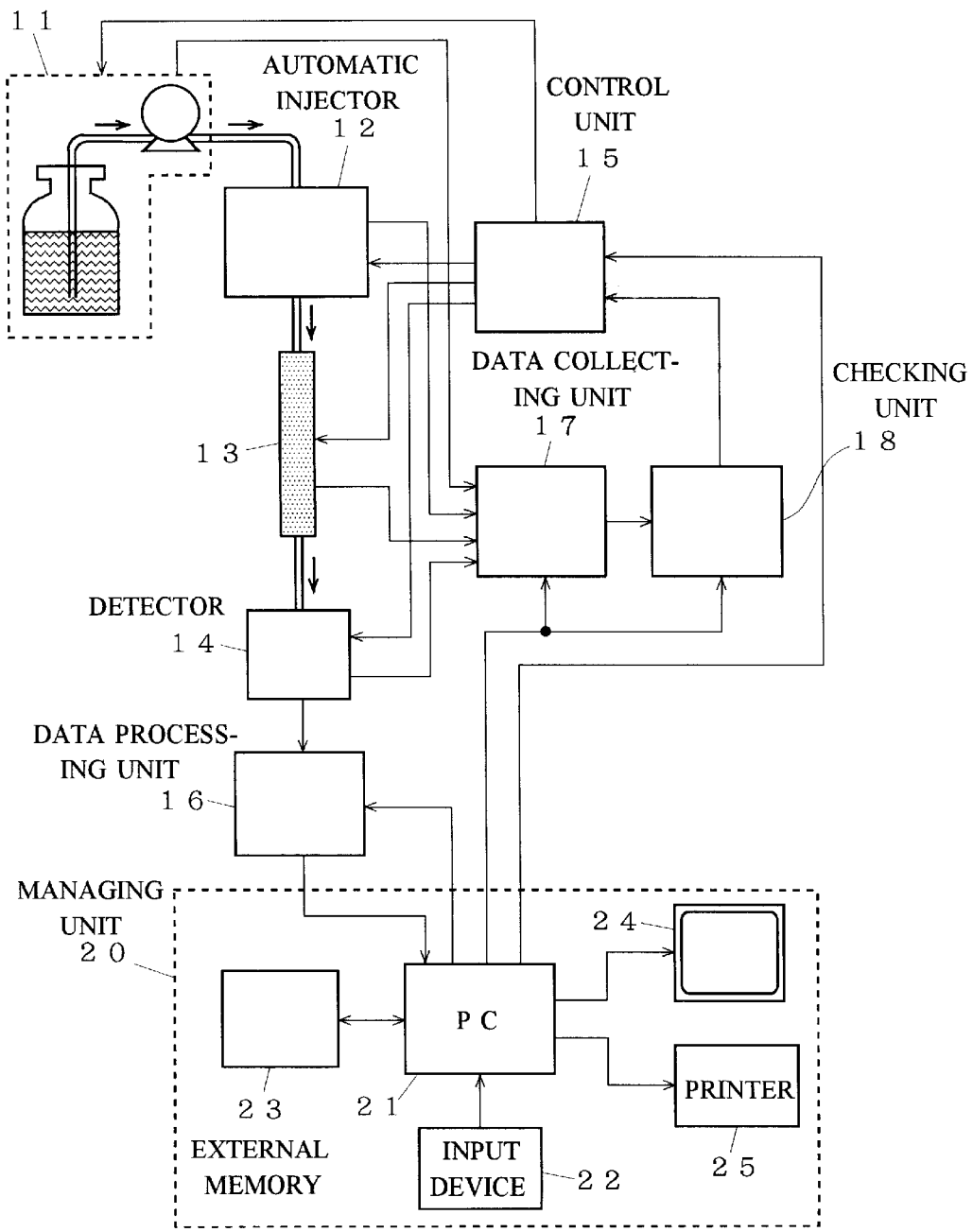
FIG. 1 is a diagram showing a schematic configuration of an LC which is an embodiment of an inventive analyzing system.

FIG. 1 shows a schematic configuration of an LC as an embodiment of the present invention. In the LC, a data collecting unit 17 collects specific signals from the liquid supply unit 11, the automatic injector 12, the column 13 and the detector 14. The signals carry information on the operation or condition of expendable parts used in the above-described units, which are sent to a checking unit 18. According to instructions from the managing unit 20, the checking unit 18 processes the signals to obtain information on the operation or condition of the expendable parts, and gives instructions to the control unit 15. Based on the instructions as well as on instruction signals from the managing unit 20, the control unit 15 controls each part of the analyzing system. The managing unit 20 includes a PC 21, an input device 22 (such as a keyboard), an external memory 23, a display 24, a printer 25, etc. The calculation by the data processing unit 16, and the operations of the data collecting unit 17 and the checking unit 18, may be performed by the PC 21.

In the present embodiment, the degrees of degradation of expendable parts are checked, where the expendable parts are the plunger seal of the pump of the liquid supply unit 11, the needle seal and syringe tip of the automatic injector 12, and the lamp of the spectrophotometric detector 14. Also checked is the wavelength displacement (or wavelength error) of the spectrophotometric detector 14. It should be obviously understood that the degree of degradation of other expendable parts may be also checked. In the present embodiment, the degree of degradation of the plunger seal is determined based on the total number of revolutions of the pump, that of the needle seal is determined based on the total number of injections by the automatic injector 12, that of the syringe tip is determined based on the total amount of liquid sucked into the syringe, and that of the lamp is determined based on the total number of illuminating hours the lamp is in use.

The steps of analysis using the above-described LC are explained as follows. At the beginning of using the LC, the operator manipulates the input device 22 to set maximum tolerable values of the degree of degradation for each of the expendable parts. For example, as for the plunger seal, the maximum tolerable value of the total number of revolutions of the pump is set at 3,000,000[revolutions]; as for the needle seal, the maximum tolerable value of the total number of injections is set at 40,000[cycles]; as for the syringe tip, the maximum tolerable value of the total amount of liquid being drawn is set at 4,500[ml]; and as for the lamp, the maximum tolerable value of the total number of illuminating hours is set at 1000[hours]. As for the wavelength error, the maximum tolerable value is set at 5[nm], for example.

Figures 2, 3:
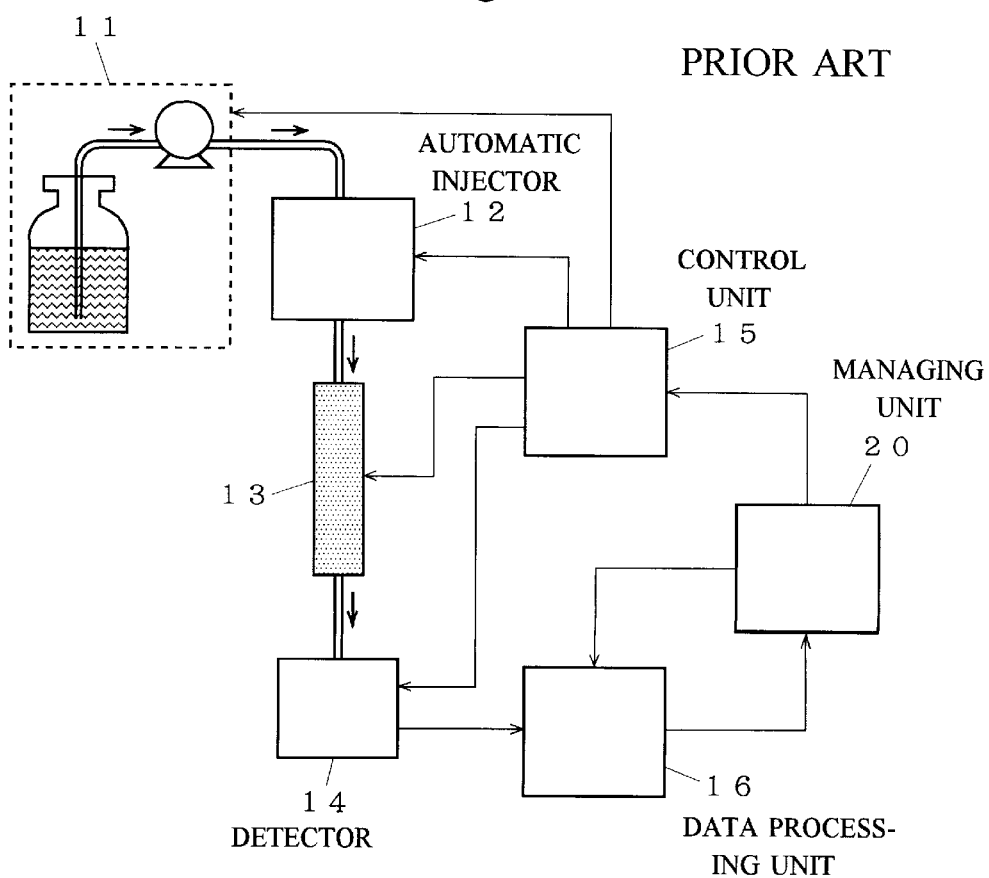
FIG. 2 is a table showing an example of an analyzing schedule.
FIG. 3 is a diagram showing a schematic configuration of a conventionally used LC.

Next, before carrying out the analysis, the operator sets up the analyzing schedule. That is, the operator manipulates the input device 22 in a predetermined manner so that a table for setting up the analyzing schedule is shown on the display 24 as shown in FIG. 2, for example. Then, using the input device 22, the operator puts data in the cells of the table. The data includes: serial number of sample; sample name; sample type (i.e. standard sample, unknown sample, control sample, etc.); name of a method file used for each analysis; instruction as to whether or not to carry out a self-check; type of a process to follow the self-check, etc. The method file contains data on the analyzing condition (e.g. the flow rate of the eluent), and is stored in a predetermined section of the external memory 23 beforehand.

In the above-described schedule, the process to follow the self-check is selected from "disregard check result", "suspend analysis on detecting abnormality" and "stop analysis on detecting abnormality". In the present embodiment, the abnormality is defined as such a situation that the wavelength error exceeds the preset tolerable limit. The analysis is neither suspended nor stopped even if the degree of degradation of an expendable part reaches the preset tolerable value of the part, and the fact is reported to the operator at the end of the analysis.

After setting up of the analyzing schedule as shown in FIG. 2, the operator manipulates the input device 22 to give an instruction to the managing unit 20, in response to which the PC 21 in the managing unit 20 starts the analysis according to the analyzing schedule. That is, the control unit 15 gives an instruction to the automatic injector 12 to select a sample of serial number 1 (which is referred to as sample No. 1 hereinafter), reads out a method file named "Sample1.Met" containing data of the analyzing condition for the sample No. 1, and controls each unit of the LC according to the analyzing condition specified in the method file. While carrying out the liquid chromatographic analysis on the sample No. 1, the detector 14 sends detection signals to the data processing unit 16. The data processing unit 16 creates a chromatogram from the detection signals, and performs waveform analysis and other calculations on the chromatogram under the processing conditions specified in the method file. The result of the analysis is saved in the external memory 23 in the form of a data file corresponding to one sample in one analysis.

The table in FIG. 2 shows that no self-check is scheduled to be carried out in the step of analyzing the sample No. 1. Therefore, after completing the analysis on the sample No. 1, the PC 21 controls each part of the LC to start the next analysis on a sample No. 2. That is, the control unit 15 gives an instruction to the automatic injector 12 to select the sample No. 2, reads out a method file named "Sample2.Met" containing data of analyzing condition for the sample No. 2, and controls each part of the LC according to the analyzing condition specified in the method file. While carrying out the analysis on the sample No. 2, the detector 14 sends detection signals to the data processing unit 16. The table in FIG. 2 shows that the self-check is scheduled to be carried out in the step of analyzing the sample No. 2. Therefore, the PC 21 gives an instruction to the checking unit 18 to start the self-check after completion of the analysis on the sample No. 2.

The total number of revolutions of the pump, the total number of illuminating hours of the lamp, etc., are monitored by the respective units throughout the analysis. The units generate signals which carry data on the degree of degradation of the expendable parts, which are sent to the data collecting unit 17. On receiving the instruction from the PC 21 to start the self-check, the checking unit 18 receives the data from the data collecting unit 17, compares the values of data to the preset tolerable values of the degree of degradation of the expendable parts, and calculates a degradation index for every expendable part by taking a ratio (percentage) of the value of the data to the maximum tolerable value, for example. Further, the checking unit 18 receives data on the wavelength error from the spectrophotometric detector 14, and determines whether the wavelength error is larger than the preset tolerable limit. If the wavelength error is larger than the tolerable limit, the checking unit 18 sends an NG (no good) signal to the control unit 15. On receiving the NG signal, the control unit 15 carries out the process specified in the analyzing schedule. For example, when the NG signal is generated during the self-check carried out immediately after the analysis on the sample No. 2, the control unit 15 controls each part of the LC so that the LC is stopped without carrying out the analysis on sample No. 3 and the subsequent samples, because the process specified to follow the detection of abnormality in this step is "stop analysis on detecting abnormality".

When the NG signal is generated during the self-check carried out immediately after the analysis on the sample No. 3, the control unit 15 controls each part of the LC to further carry out the analysis on sample No. 4 and the subsequent samples, because the process specified to follow the detection of abnormality in this step is "disregard check result". When the NG signal is generated during the self-check carried out immediately after the analysis on the sample No. 4, the control unit 15 controls each part of the LC to be ready for the next analysis on a sample No. 5, because the process specified to follow the detection of abnormality in this step is "suspend analysis on detecting abnormality". In this case, the operator gives an instruction to the control unit 15 as to whether to stop or to continue the analysis. On receiving the instruction, the control unit 15 either stops the analysis completely or further continues the analysis on sample No. 5 and the subsequent samples.

After completing all the analyses on the samples according to the analyzing schedule, the control unit 15 stops the operations of each part of the LC. Then, the control unit 15 makes a printed report with the printer 25, where the report contains the results of the checks carried out during the analysis as well as the results of the analysis. That is, if the degree of degradation of an expendable part reaches the maximum tolerable value of the part during the analysis, the name of the expendable part and the step in which the above-described tolerable value is reached, are printed out in the report. Thus, the operator can easily judge that at least the results of analysis obtained before the step printed out in the report are reliable, and only the analysis after the step should be carried out again, if necessary.

In the above-described embodiment, the self-check is carried out immediately after the analysis on each sample. It is of course possible to carry out the self-check just before the analysis on each sample. The timing to carry out the self-check (i.e. before or after the analysis of each sample) may be determined also in the analyzing schedule.

In the above-described embodiment, only a situation where the wavelength error exceeds the preset tolerable limit, is regarded as abnormal, and not a situation where the degree of degradation of an expendable part reaches the maximum tolerable value of the part. It is of course possible to regard also the latter situation as abnormal. Further, it is possible to regard latter situation as abnormal only with respect to some specific expendable parts.

As described above, while a series of analyses are continuously carried out with the inventive analyzing system for a long period of time, the analysis is either suspended or stopped automatically according to the preset analyzing schedule such as in the case where an abnormality occurs to a part of the analyzing system or that the error of a detector or the like becomes abnormally large. Therefore, when all the analyses have been completed without being suspended or stopped, it means that the analyzing system had operated correctly throughout the analyses and, accordingly, the results of the analyses are reliable. Further, the inventive analyzing system is advantageous in saving time and resources (samples, eluent, etc.) because such fruitless analysis that yields only unreliable results is avoided assuredly.

Finally, it should be understood that the above embodiment is a mere example, and the present invention can be embodied in other forms within the true spirit and scope thereof.

What is claimed is:

1. An analyzing system for carrying out a series of analyses on a plurality of samples according to a predetermined analyzing schedule, comprising:
   a) input means for allowing an operator to set the analyzing schedule, where the analyzing schedule includes an option whether or not to carry out a check at an analysis on each of the plurality of samples, and an option of a process to follow the check according to a result of the check;
   b) checking means for checking a state of a part in the analyzing system at an analysis of a sample at which the check is scheduled to be carried out; and
   c) control means for receiving a result of the check from the checking means, and for performing the process specified in the analyzing schedule.

2. The analyzing system according to claim 1, wherein the checking means checks the state of the part before the analysis of a sample at which the check is scheduled to be carried out.

3. The analyzing system according to claim 1, wherein the checking means checks the state of the part after the analysis of a sample at which the check is scheduled to be carried out.

4. The analyzing system according to claim 1, wherein an option of a process specified in the analyzing schedule is to stop a following analysis when it is found from the result of the check that an abnormality is detected.

5. The analyzing system according to claim 1, wherein an option of a process specified in the analyzing schedule is to suspend a following analysis when it is found from the result of the check that an abnormality is detected.

6. The analyzing system according to claim 1, wherein an option of a process specified in the analyzing schedule is to carry out a following analysis even when it is found from the result of the check that an abnormality is detected.

7. The analyzing system according to claim 1, comprising a spectrophotometric detector, wherein the checking means checks a displacement of wavelength of the spectrophotometric detector from a desired wavelength preset by the operator.

8. The analyzing system according to claim 7, wherein the checking means further checks a degree of degradation of at least one of mechanically expendable parts of the analyzing system, and an option of a process specified in the analyzing schedule is to stop a following analysis when the displacement of wavelength is larger than a preset value, irrespective of results of the checks on said at least one of mechanically expendable parts.

9. The analyzing system according to claim 1, wherein the input means includes display means for displaying a table for setting the analyzing schedule.

10. The analyzing system according to claim 1, further comprising reporting means for reporting the operator of the result of the check carried out by the checking means.

* * * * *